United States Patent [19]

Jacques

[11] Patent Number: 4,605,006
[45] Date of Patent: Aug. 12, 1986

[54] HYPOTHERMIC PROTECTION PAD

[75] Inventor: Roberta C. Jacques, West Lakeland Township, Washington County, Minn.

[73] Assignee: Minnesota Mining and Manufacturing Company, St. Paul, Minn.

[21] Appl. No.: 584,316

[22] Filed: Feb. 28, 1984

[51] Int. Cl.$^4$ .............................................. A61F 7/12
[52] U.S. Cl. .................................... 128/401; 62/530; 128/402; 128/403
[58] Field of Search ............... 128/400, 402, 403, 401; 62/530

[56] References Cited

U.S. PATENT DOCUMENTS

| | | | |
|---|---|---|---|
| 543,177 | 7/1895 | Daly | 128/400 X |
| 3,738,372 | 6/1973 | Shioshuili | 128/400 |
| 3,874,504 | 4/1975 | Verakas | 206/219 |
| 3,888,259 | 6/1975 | Miley | 128/400 |
| 3,889,684 | 6/1975 | Lebold | 128/403 X |
| 3,893,834 | 7/1975 | Armstrong | 128/403 X |
| 4,049,408 | 9/1977 | Patel | 128/403 X |
| 4,118,531 | 10/1978 | Hauser | 428/224 |
| 4,154,245 | 5/1979 | Daily | 128/400 |
| 4,259,961 | 4/1981 | Hood, III | 128/400 |
| 4,474,016 | 10/1984 | Winchell | 62/530 |

FOREIGN PATENT DOCUMENTS 2497934 7/1982 France .................................. 128/403

OTHER PUBLICATIONS

"Topical Cardiac Cooling by Recirculation: Comparison of a Closed System Using a Cooling Pad with an Open System Using a Topical Spray", by Rosenfeld and Arnold, The Annals of Thoracic Surgery, 34(2), pp. 138-145, 1982.
"Shiley Cardiac Insulation Pad", literature, copyright 1980, three sheets.
"3M Coldhot Pack Tips", literature, undated, two sheets.

*Primary Examiner*—Anton O. Oechsle
*Attorney, Agent, or Firm*—Donald M. Sell; James A. Smith; Robert W. Hoke, II

[57] ABSTRACT

A hypothermic protection pad for topically cooling an internal organ. The pad includes a flexible outer pouch, a flexible bladder within the pouch, a biocompatible liquid within the bladder and a thermal insulating layer within the pouch and adjacent one side of the bladder. Methods of achieving hypothermic protection of internal organs with cooling pads are also included.

7 Claims, 13 Drawing Figures

HYPOTHERMIC PROTECTION PAD

BACKGROUND

The invention relates to the field of cooling pads for hypothermic protection of internal organs during surgery, organ transplant and the like. Methods of achieving hypothermic protection of internal organs with cooling pads are also included within the scope of the invention.

Ischemic damage to organs is a serious concern during many types of cardiovascular surgeries, organ transplants and the like. Ischemic damage is caused by the blood supply being insufficient to meet the metabolic needs of the affected organ. It is a form of local anemia. A known method of minimizing or avoiding ischemic damage is to cool the affected organ. Cooling greatly reduces the organ's rate of metabolism, and consequently, its need for oxygenated blood.

Various methods and devices have been developed to cool organs and avoid ischemic damage. A leading example is the use of cold cardioplegic solution to arrest and to cool the heart during open heart surgery to reduce its metabolic requirements. The cardioplegic solution is infused into the root of the aorta or directly into the coronary arteries. It circulates through the coronary arteries and the coronary veins, and eventually drains into the right atrium of the heart through the coronary sinus.

Another example is topical cooling of the heart. This is typically performed during open heart surgery in combination with infused cardioplegia to protect the myocardium between infusions. Topically cooling involves externally contacting at least a portion of the heart with a cold fluid or a cold surface. Topically cooling is used to augment other means of achieving hypothermia of the heart. A topical spray is described in "Topical Cardiac Cooling by Recirculation: Comparison of a Closed System Using a Cooling Pad with an Open System Using a Topical Spray," by Franklin I. Rosenfeldt and Malcolm Arnold, The Annals of Thoracic Surgery, 34(2), 138-145, 1982. A cooled saline solution is sprayed on the heart, collected, recooled and sprayed on the heart again. Another example is the use of a cooling pad through which a cooling fluid is circulated. As with the topical spray, a saline solution is cooled, brought into heat exchange relationship with the heart, recooled, and the process repeated. Such a pad is disclosed in U.S. Pat. No. 4,259,961. A similar pad for a kidney is disclosed in U.S. Pat. No. 3,738,372, and one for an entire body is disclosed in U.S. Pat. No. 3,888,259. Each of the prior art sprays and pads require an external source of cooling during use on the organ. These external heat exchangers and their connecting tubing are bulky and cumbersome in an already crowded surgical field.

Another example of topically cooling is the use of a thermal pack marketed by Minnesota Mining and Manufacturing Company, St. Paul, Minn. It contains a gel comprised of 70 weight percent water, 25 weight percent propylene glycol and 5 weight percent hydroxypropyl methylcellulose. It is not, however, recommended for such use by Minnesota Mining and Manufacturing Company.

Efforts have been made to avoid rewarming of the heart between infusions of cardioplegic solutions with passive insulation pads. Such a pad is marketed by Shiley Inc., Irvine, Calif. It is described as thin and pliable to conform to the heart and made of polyethylene foam. It is said to insulate the myocardium from the warmer descending thoracic and surrounding pericardial tissues. As a passive device, the pad must be used in combination with some form of active cooling. Typically, the pad is placed between the heart and the pericardium. The heart is then surrounded by an ice slush to provide the active cooling.

SUMMARY OF THE INVENTION

According to the invention, there is provided a hypothermic protection pad for topically cooling an internal organ. The pad comprises a flexible outer pouch, a flexible bladder disposed within the pouch, a biocompatible liquid contained within the bladder and a thermal insulating layer disposed within the pouch. The pouch has two major, opposite sidewalls. The bladder also has two major, opposite sidewalls and is disposed between the sidewalls of the pouch. The thermal insulating layer is disposed between one sidewall of the pouch and one sidewall of the bladder so that the hypothermic protection pad can be positioned between the internal organ and a surface with the insulation layer between the bladder and the surface. This restricts heat transfer from the surface into the liquid while permitting heat transfer from the internal organ into the liquid. In one embodiment, the thermal insulating layer is comprised of a web of microfibers and crimped bulking fibers.

According to the invention, there is also provided a method of cooling an internal organ. The method comprises the steps of providing a sterilized hypothermic protection pad, cooling the pad to a predetermined temperature and positioning the pad between the organ and a surface or receiving the organ within the pad. In one embodiment, the pad comprises a flexible outer pouch, a flexible inner bladder disposed with the pouch, a biocompatible liquid contained within the bladder and a thermal insulating layer disposed within the pouch. The pouch has two major, opposite sidewalls. The bladder also has two major, opposite sidewalls and is disposed between the sidewalls of the pouch. The thermal insulating layer is disposed between one sidewall of the pouch and one sidewall of the bladder so that the insulation layer is between the bladder and the surface when the hypothermic protection pad is positioned between the internal organ and the surface. This restricts heat transfer from the surface into the liquid while permitting heat transfer from the internal organ into the liquid.

The term "biocompatible" as used herein to describe the liquid means the liquid is nontoxic and compatible with animal tissue.

BRIEF DESCRIPTION OF THE DRAWINGS

Other advantages of the invention will become apparent from the following drawings wherein like numbers refer to like parts, the accompanying description and the appended claims.

DESCRIPTION

Figure 1:
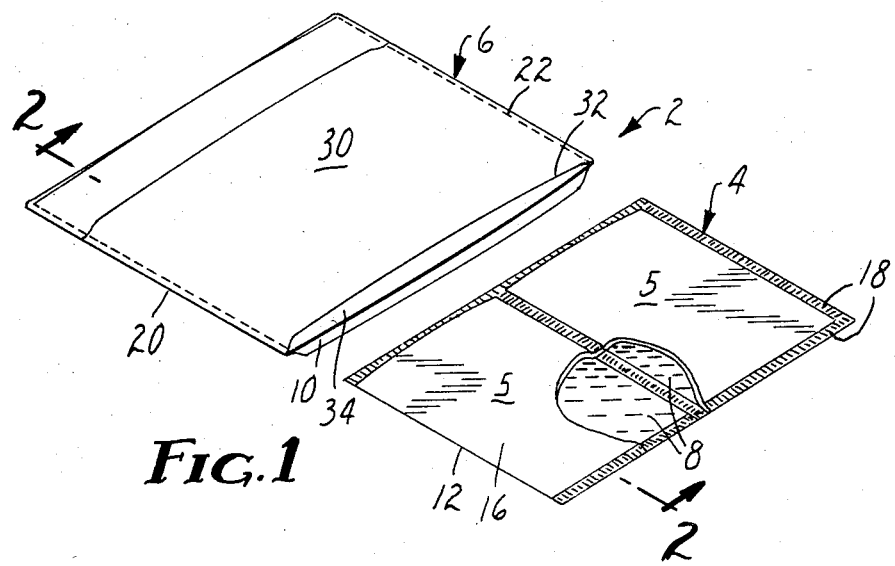
FIG. 1 is a perspective view of one unassembled embodiment of a hypothermic protection pad of the present invention.

Referring now to FIG. 1 of the drawings, there is shown a perspective view of one unassembled embodiment of a hypothermic protection pad 2. The pad 2 is generally comprised of an inner cooling bladder 4 and an outer pouch 6. The inner pouch 4 contains a predetermined amount of a biocompatible liquid 8 capable of absorbing and dissipating heat. The outer pouch 6 includes a thermal insulating layer 10.

Figure 2:
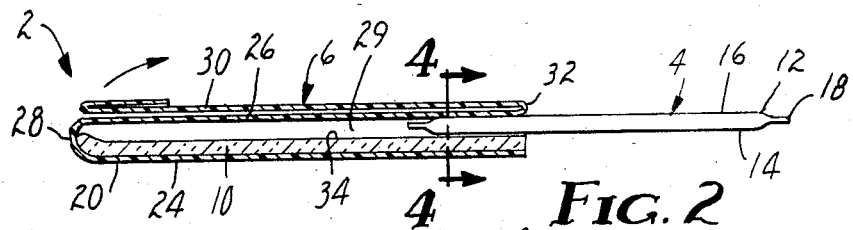
FIG. 2 is a cross-sectional view of the hypothermic protection pad of FIG. 1 taken along line 2—2 of FIG. 1 partially assembled.

As shown in FIG. 1 and FIG. 2, the inner pouch 4 comprises a sheet 12 of flexible, liquid-tight material that is folded over to define a first major sidewall 14 and a second major sidewall 16. One such material is "Saranex" 15 brand, low-density polyethylene/polyvinylidene chloride/low-density polyethylene laminate available from Dow Chemical Company, Midland, Mich. Another is "Scotchpak" brand heat sealable polyester film, available from Minnesota Mining and Manufacturing Company. The sheet 12 is peripherally sealed to itself by a mechanically strong heat seal 18. The heat seal 18 is extended across the midsection of the bladder 4 to divide the bladder 4 into two smaller bladders 5. These smaller bladders 5 each contain a portion of the biocompatible liquid 8 and restrict pooling of the liquid 8. Pooling of the liquid 8 can result in an uneven distribution of the liquid 8, thereby compromising the efficacy of the pad 2.

Within the inner pouch 4 is contained the biocompatible liquid 8. One such liquid is a saline solution comprised of sodium chloride in water. The preferred liquid is a sterile, isotonic solution of sodium chloride in water. It contains not less than 0.85 weight percent and not more than 0.95 weight percent of sodium chloride. The most preferable liquid is known as 0.89 weight percent USP saline. It is defined in United States Pharmacopeia XIX, pages 456–457.

Figure 3:
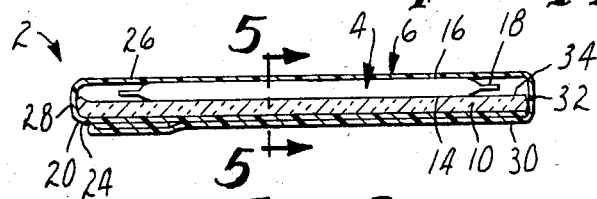
FIG. 3 is a cross-sectional view of the hypothermic protection pad of FIG. 2 fully assembled.

The inner bladder 4 containing the liquid 8 is received within the outer pouch 6 as shown in FIG. 2 and FIG. 3. The outer pouch 6 is generally comprised of an overwrap 20 and the thermal insulating layer 10. The overwrap 20 can be any of a number of thin fabrics and films. Flexible, polymeric films are generally preferred. Ethylene methyl acrylate films are most preferred. Nonwoven fabrics work well because of their nontoxic, nonlinting and nonslip characteristics. A suitable nonwoven fabric is "Sontara" brand spun-laced fabric available from E. I. DuPont De Nemours & Co. (Inc.), Wilmington, Del. Another suitable material is "Evolution" brand spun-bonded polypropylene available from Kimberly-Clark Corporation, Neenah, Wis.

The insulating layer 10 is preferably comprised of a web of microfibers. Microfibers are very fine, discontinuous fibers typically prepared by extruding liquified fiber-forming material through orifices in a die into a high-velocity gaseous stream. The extruded material is first attenuated by the gaseous stream and then solidified as a mass of fibers. Representative polymers for forming melt-blown microfibers include polypropylene, polyethylene, polyethylene terephthalate, polyamides and other polymers as known in the art. The insulating layer 10 is most preferably comprised of a web of microfibers and crimped bulking fibers. Crimped bulking fibers are those having a continuous wavy, curly, or jagged character along their length as shown in FIG. 2A, FIG. 2B and FIG. 2C of U.S. Pat. No. 4,118,531. As more fully described in U.S. Pat. No. 4,118,531 which is hereby incorporated by reference, mixtures of microfibers and crimped bulking fibers produce lofty resilient webs having high thermal resistance per unit of thickness and moderate weight. A distinct advantage of such webs over other insulation materials in the present invention is that they maintain their insulating ability when wet. These and other properties give these webs unique utility as thermal insulation. The most preferred web is "Thinsulate Composite" brand insulation, type C-200, available from Minnesota Mining and Manufacturing Company. It is comprised of about 65 weight percent polypropylene blown microfiber and 35 weight percent, 6 denier/filament polyester crimped bulking fiber.

The insulating layer 10 is preferably attached to the overwrap 20 at peripheral seams or seals 22. Seams or seals 22 are suitably made by conventional sewing, ultrasonic sealing, heat sealing or the like. Seams or seals 22 can also be seen in FIG. 4 and FIG. 5.

As shown in FIGS. 2, 3, 4 and 5, a single piece of overwrap 20 is preferably used in the construction of the outer pouch 6. Referring to FIG. 2, the overwrap 20 is comprised of a first major sidewall 24 connected to a second major sidewall 26 by a first curved portion 28 to define a compartment 29. A third major sidewall 30 is connected to the second major side 26 by a second curved portion 32. The inner cooling bladder 4 is disposed within the compartment 29. This juxtaposes the first major sidewall 14 of the inner bladder 4 and a first major surface 34 of insulating layer 10 and thermally insulates the inner bladder 4 from the sidewall 24.

Once the inner bladder 4 is disposed within outer pouch 4, assembly of hypothermic protection pad 2 is completed by folding sidewall 30 of the overwrap 20 over the sidewall 24 as depicted by an arrow in FIG. 2. It results in the protection pad construction shown in FIG. 3. The sidewall 30 of the overwrap 20 is moved from adjacent the sidewall 26 to adjacent the sidewall 24, leaving the sidewall 26 exposed. The curved portion 32 is inverted and retains the inner bladder 4 within the pad 2. At the same time, the seams or seals 22 are hidden within the overwrap 20 as best seen in FIG. 5.

Figure 4:
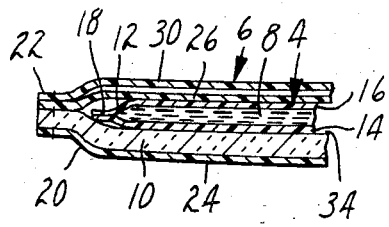
FIG. 4 is an enlarged, fragmentary view of the hypothermic protection pad of FIG. 2 taken along the line 4—4 of FIG. 2.
Figure 5:
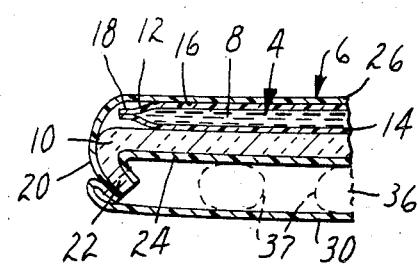
FIG. 5 is an enlarged, fragmentary view of the hypothermic protection pad of FIG. 3 taken along the line 5—5 of FIG. 3.

The manner in which seams or seals 22 are turned from the outside to the inside is shown in FIGS. 4 and 5. FIG. 4 is an enlarged, fragmentary view of the hypothermic protection pad of FIG. 2. It shows the sidewall 30 adjacent the sidewall 26. FIG. 5 illustrates the seams or seals 22 turned in or reversed, and the sidewall 30 juxtaposed the sidewall 24 to define a glove 36 adapted to accommodate a hand 40, shown in FIG. 6, and depicted in in FIG. 5 in phantom line representation as fingers 37.

Figure 6:
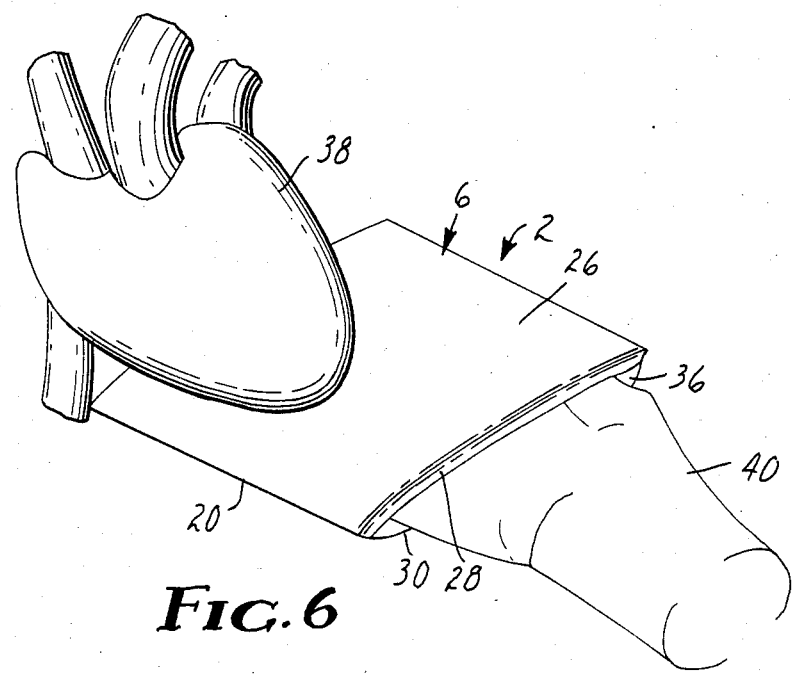
FIG. 6 is a perspective view of the hypothermic protection pad of FIG. 1. fully assembled and being positioned adjacent a heart.
Figure 7:
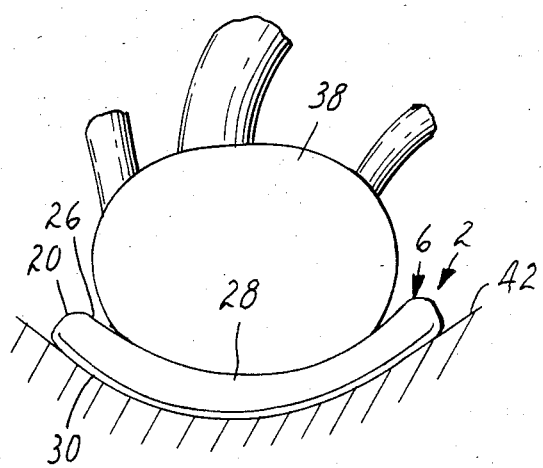
FIG. 7 is an end view of the hypothermic protection pad of FIG. 6 positioned between the heart and a body portion.

A method of cooling an internal organ with the hypothermic protection pad 2 will next be described in conjunction with FIGS. 6 and 7. Referring first to FIG. 6, the pad 2 is shown being contacted with a heart 38 by the hand 40. The hand 40 is inserted within the glove 36. The pad 2 is contacted with the heart 38. The heart 38 is brought to rest against a surface 42, typically a pericardial cavity, with the pad 2 positioned between the heart 38 and the surface 42 as shown in FIG. 7. In this position, the heart 38 can be cooled by the bladder 4 within the pad 2, and the inner bladder 4 is thermally insulated from the surface 42 by the insulating layer 10 within the pad 2.

The hypothermic protection pad 2 must be suitably cooled and sterilized prior to use. The temperature to which it is cooled and the cooling capacity required for any particular application are matters of individual medical judgment based on training and experience. A generally accepted temperature for cardiac cooling during open heart surgery is approximately 4° C. Hence, a starting temperature of approximately 4° C. for pad 2 is believed to be appropriate for this application. The pad can be suitably sterilized by conventional gamma radiation of the outerwrap 20 and ethylene oxide gas treatment of the liquid 8.

The pad 2 of the present invention preferably contains about 140 gm of 0.89 weight percent, USP saline and includes 40 gm/m$^2$–300 gm/m$^2$ and preferably 200 gm/m$^2$ of "Thinsulate Composite", type C-200 insulation in the insulating layer 10. The inside dimensions of the bladder 4 preferably are about 3½ inches by about 6½ inches. The insulating layer 10 preferably measures about 4¼ inches by about 6¾ inches. The bladder 4 is preferably comprised of "Saranex" 15 brand, low-density polyethylene/polyvinylidene chloride/low-density polyethylene laminate available from the Dow Chemical Company, and the outerwrap 20 is preferably comprised of an ethylene methyl acrylate film.

Figure 10:
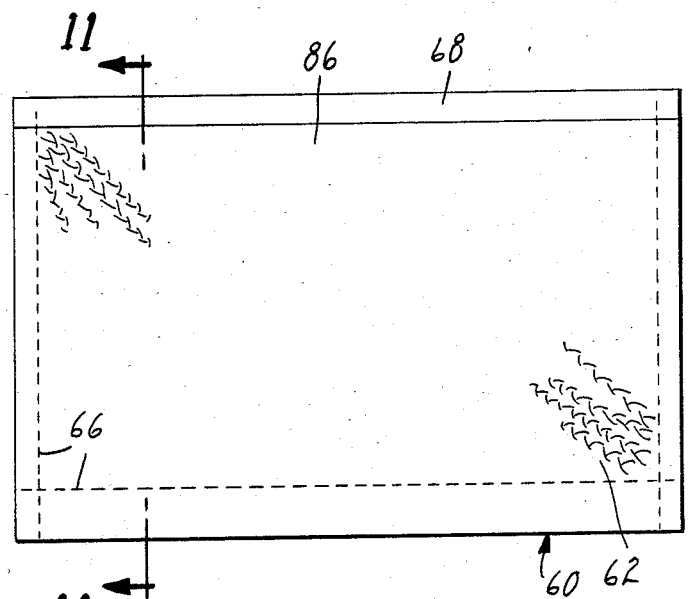
FIG. 10 is a plan view of an alternate embodiment of an outer pouch that can receive the inner cooling bladder of FIG. 1 or FIG. 8.
Figure 11:
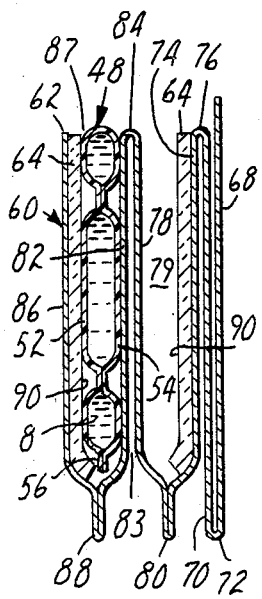
FIG. 11 is a cross-sectional view of the outer pouch of FIG. 10 taken along the line 11—11 of FIG. 10 and including the inner cooling bladder of FIG. 8 disposed within one of two outer compartments.
Figure 12:
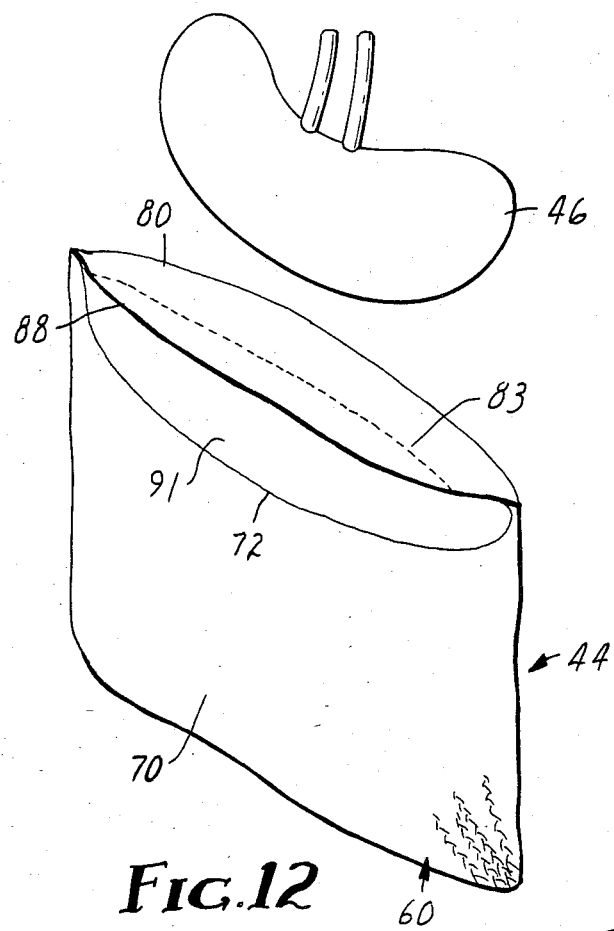
FIG. 12 is a perspective view of an alternate embodiment of a hypothermic protection pad assembled from the outer pouch of FIG. 10 and two of the inner cooling bladders of FIG. 8 shown receiving a kidney within a central pocket.
Figure 13:
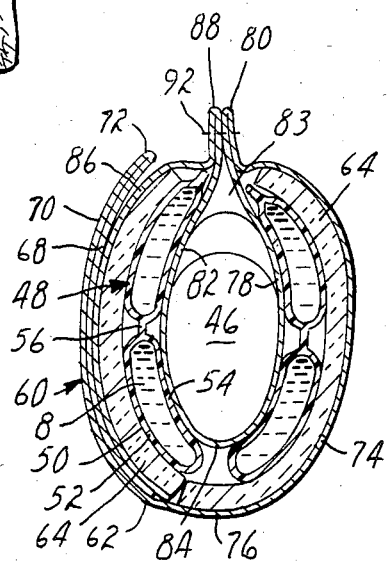
FIG. 13 is a cross-sectional view of the hypothermic protection pad and kidney of FIG. 12.

FIGS. 8–13 illustrate an alternate hypothermic protection pad 44 of the present invention that is particularly well suited for protecting an organ that has been removed as, for example, in the case of an organ transplant when the donor and the recipient are often a considerable distance apart. FIGS. 12 and 13 depict a kidney 46 being received and protected within the alternate hypothermic cold pad 44.

Figure 8:
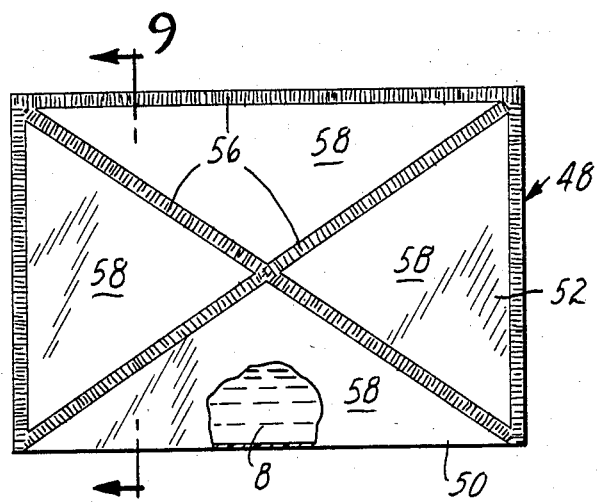
FIG. 8 is a plan view of an alternate embodiment of an inner cooling bladder that can be used in the hypothermic protection pad of FIG. 1.
Figure 9:
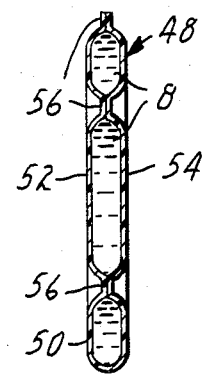
FIG. 9 is a cross-sectional view of the inner cooling bladder of FIG. 8 taken along the line 9—9 of FIG. 8.

Referring specifically to FIGS. 8 and 9, there is shown an alternate inner cooling bladder 48 that can be used in the hypothermic protection pad 2 of FIGS. 1–7 as well as in the pad 44 of FIGS. 8–13. As with the inner bladder 4, the inner bladder 48 comprises a sheet 50 of flexible, liquid-tight material that is folded over to define a first major sidewall 52 and a second major sidewall 54. The sheet 50 is peripherally sealed to itself by a mechanically strong heat seal 56. The heat seal 56 is extended across the midsection of the bladder 48 to divide the bladder 48 into a number of smaller bladders 58. These smaller bladders 58, each containing the biocompatible liquid 8, prevent the liquid 8 from pooling when the bladder 48 is used in different applications. One such application is shown in FIG. 13. Without the aid of smaller bladders 58, the liquid 8 could unevenly distribute and compromise the efficacy of the pad 2.

FIG. 10 is a plan view of an alternate embodiment of an outer pouch 60 that can receive inner bladder 4 or inner bladder 48. Inner bladder 48 is preferably used with outer pouch 60.

As with outer pouch 6, outer pouch 60 is generally comprised of an overwrap 62 and, in this case, a pair of insulating layers 64 as best seen in FIG. 13. The overwrap 62 can be of the same materials as overwrap 20. The overwrap 62 is preferably comprised of a nonwoven fabric, and most preferably is comprised of the "Sontara" brand spun-laced fabric identified earlier. The insulating layers 64 are preferably of the same microfibers and crimped bulking fibers as insulation pad 10. The insulation pads 64 are suitably attached to the overwrap 62 as before by peripheral seams or seals 66.

As shown in FIG. 11, a single piece of overwrap 62 is used in the construction of the outer pouch 60. The overwrap 62 is comprised of a first major sidewall 68 attached to a second major sidewall 70 by a first curved portion 72. A third major sidewall 74 is connected to the second major sidewall 70 by a second curved portion 76. A fourth major sidewall 78 is connected to the third major sidewall 74 by a third curved portion 80 to define a compartment 79. A fifth major sidewall 82 is connected to the fourth major sidewall 78 by a fourth curved portion 84 to define a receiving pocket 83. A sixth major sidewall 86 is connected to the fifth major sidewall 82 by a fifth curved portion 88 to define a compartment 87. The two inner bladders 48 are disposed within the outer pouch 60 with one bladder 48 within compartment 79 and one bladder 48 within compartment 87. This juxtaposes the first major sidewalls 52 of the inner bladders 48 and a first major surface 90 of each insulation pad 64 and insulates the inner bladders 48 from the sidewalls 74 and 86 of the outerwrap 62.

Once the inner bladders 48 are disposed within the outer pouch 60, assembly of hypothermic protection pad 44 is completed by folding sidewalls 68 and 70 over sidewall 86 as shown in FIG. 13. This is accomplished in the same manner as described in relation to FIG. 2 for the pad 2. The result is sidewall 68 is juxtaposed sidewall 86, and sidewall 74 is now exposed. At the same time, the second curved portion 76 is drawn across inner bladders 48 to retain them within the hypothermic protection pad 44.

The method by which hypothermic protection pad 44 is contacted with an organ, depicted in FIGS. 12 and 13 as the kidney 46, will next be described in conjunction with FIGS. 12 and 13. Referring first to FIG. 12, the kidney 46 is received within the pocket 83. As in the case of hypothermic protection pad 2, two of the sides, in this case sides 68 and 86, define a glove 91 that can be used to assist in positioning the pad 44 for reception of the kidney 46.

Once the kidney 46 is fully received as shown in FIG. 13, the third curved portion 80 and the fifth curved portion 88 of overwrap 62 are preferably drawn together by a seam or seal 92. This draws inner bladders 48 against kidney 46 through sides 78 and 82 of outerwrap 62, reduces thermal gains between curved portions 80 and 88 of outerwrap 62 and prevents the kidney 46 from being unintentionally dislocated from the pad 44.

As with the pad 2, the pad 44 must be suitably cooled and sterilized prior to use. A starting temperature of about 4° C. is again preferred. The pad 44 preferably contains about 100 gm of 0.89 weight percent, USP saline per inner bladder 48 and includes 40 gm/m$^2$–300 gm/m$^2$ and preferably 200 gm/m$^2$ of "Thinsulate Composite", type C-200 insulation per insulating layer 64. The inside dimensions of the bladders 48 preferably are about 3¾ inches by about 5¾ inches. The insulating layers 10 preferably measure about 4 inches by about 6 inches. The bladders 48 are preferably comprised of "Saranex" 15 brand laminate as identified earlier, and the overwrap 62 is preferably comprised of "Sontara" brand spun-laced fabric as identified earlier.

What is claimed is:

1. A hypothermic protection pad for topically cooling an internal organ comprising:
   A. a flexible, outer pouch, comprised of a polymeric film and having two major, opposite sidewalls;
   B. a flexible liquid-tight bladder having two major, opposite sidewalls, said bladder being disposed within said pouch between said sidewalls of said pouch;
   C. a sterile solution of sodium chloride in water, containing 0.85–0.95 weight percent of sodium chloride, capable of absorbing and dissipating heat and contained within said bladder; and
   D. a thermal insulating layer comprising a web of microfibers, said layer being disposed within said pouch between one sidewall of said pouch and one sidewall of said bladder so that said hypothermic protection pad can be positioned between said internal organ and a surface with said insulation layer between said bladder and said surface to restrict heat transfer from said surface into said liquid while permitting heat transfer from said organ into said liquid.

2. The protection pad according to claim 1 wherein said insulating layer is attached to said outer pouch.

3. The protection pad according to claim 3 further comprising polymeric film means for handling said outer pouch peripherally attached to a major outside surface of said one sidewall of said outer pouch opposite said insulating layer and defining a glove adapted to slideably receive a hand of a user and to aid in contacting said pad with said organ.

4. The protection pad according to claim 3 wherein said saline solution comprises about 0.89 weight percent of sodium chloride.

5. The protection pad according to claim 4 wherein said web further comprises crimped bulking fibers.

6. The protection pad according to claim 5 wherein said bladder contains about 140 gm of said saline solution and said web includes 40 gm/m$^2$–300 gm/m$^2$ of said microfibers and said crimped bulking fibers.

7. A method of topically cooling an internal organ comprising the steps of:
   A. providing a sterilized hypothermic protection pad according to claim 1;
   B. cooling said protection pad to about 4° C.; and
   C. positioning said hypothermic protection pad between said internal organ and a surface with said insulation layer between said bladder and said surface to restrict heat transfer from said surface into said liquid while permitting heat transfer from said organ into said liquid.

* * * * *

UNITED STATES PATENT AND TRADEMARK OFFICE
CERTIFICATE OF CORRECTION

PATENT NO. : 4,605,006
DATED : August 12, 1986
INVENTOR(S) : Roberta C. Jacques (Roberta Collins Harper)

It is certified that error appears in the above—identified patent and that said Letters Patent is hereby corrected as shown below:

Col. 2, line 68, "assembled. FIG. 4 is" should read --assembled. FIG. 4 is--

Col. 8, line 8, "according to claim 3" should read --according to claim 2--.

Front page of patent, inventor is shown as "Roberta C. Jacques"; should read —Roberta Collins Harper—

Signed and Sealed this

Eleventh Day of November, 1986

Attest:

DONALD J. QUIGG

Attesting Officer     Commissioner of Patents and Trademarks